US00PP27024P3

(12) United States Plant Patent
Olesen

(10) Patent No.: US PP27,024 P3
(45) Date of Patent: Aug. 9, 2016

(54) MINIATURE ROSE PLANT NAMED 'POULPAH071'

(50) Latin Name: *Rosa hybrid*
Varietal Denomination: Poulpah071

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 14/121,265

(22) Filed: Aug. 15, 2014

(65) Prior Publication Data

US 2016/0050811 P1 Feb. 18, 2016

(51) Int. Cl.
*A01H 5/02* (2006.01)

(52) U.S. Cl.
USPC ..... Plt./122

(58) Field of Classification Search
USPC ..... Plt./122, 129
CPC ..... A01H 5/0222; A01H 5/0216
See application file for complete search history.

(56) References Cited

PUBLICATIONS http://www.poulsenroser.dk/media/73602/PATIOHIT-Outdoor-2013_LR_Poulsen-Roser.pdf; 2012; 1 page.*

* cited by examiner

*Primary Examiner* — Kent L Bell

(57) ABSTRACT

A new garden rose plant of the Miniature class which has abundant, red flowers and attractive foliage. This new and distinct variety has shown to be uniform and stable in the resulting generations from asexual propagation.

1 Drawing Sheet

Botanical designation: *Rosa* hybrid.
Variety denomination: 'Poulpah071'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2006 and the resulting seeds were planted in a controlled environment in Fredensborg, Denmark. The new variety, named 'Poulpah071', originated as a single seedling from the stated cross.

The new variety may be distinguished from its male pollen parent and female seed parent primarily by the following characteristics. The female seed parent has orange red flowers, while the new variety has red flowers. The male pollen parent is about 40 cm in growth height, while the new variety is 20-25 cm in height.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpah071' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulpah071' was selected in the spring of 2007 by the inventor as a single plant from the progeny of the aforementioned hybridization.

Asexual reproduction of 'Poulpah071' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poulpah071' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah071'.

Specifically illustrated in the drawing are a flowering branch, flower in parts, leaves, and stems. Plants shown are 2 years of age.

DETAILED DESCRIPTION OF THE VARIETY

The following is a description of 'Poulpah071', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah053', U.S. Plant Pat. No. 24,090 are compared to 'Poulpah071' in Chart 1.

CHART 1

| | 'Poulpah071' | 'Poulpah053' |
|---|---|---|
| Petal Count | 40 | 30 |
| Flower Diameter | 50 mm | 45 mm |
| General Tonality of Flower Color | Red Group 46B | Red Group 53B |

Flower and Flower Bud

Blooming habit: Continuous.

Flower bud:

*Size.*—Upon opening, 23 mm in length from base of receptacle to end of bud. Bud diameter is 15 mm.

*Bud form.*—Ovoid.

*Bud color.*—As sepals divide petals are Red Group 53A.

*Sepal inner surface.*—Color: Yellow-Green Group 144B with light intonations of Greyed-Red Group 179B. Surface: Lightly pubescent.

*Sepal outer surface.*—Color: Yellow-Green Group 144A with strong intonations of Greyed-Purple Group 187A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—25 mm long, 10 mm wide.

*Receptacle.*—Texture: Smooth. Size: 8 mm in height, 10 mm wide. Color: Yellow-Green Group 144B with strong intonations of Greyed-Purple Group 187B. Shape: Campanulate.

*Pedicel.*—Surface: Smooth. Length: About 40 mm. Diameter: 2 mm on average. Color: Yellow-Green Group 144C with strong intonations of Greyed-Purple Group 185B. Strength: Strong.

*Peduncle.*—Length: About 3 cm. Diameter: 4 mm. Color: Yellow-Green Group 144B with intonations of Greyed-Purple Group 185B.

Flower bud development: Flower buds are borne singly and in clusters of 3 to 7 flower buds per stem.

Flower bloom:

*Fragrance.*—Light floral.

*Duration.*—The blooms have a duration on the plant of approximately 14 days. Petals fall cleanly away from plant after flowers have fully matured.

*Size.*—Flower diameter is 50 mm when open. Flower depth is 20 mm.

*Flower shape.*—High centered, semi double, with a high pointed center which is tightly closed.

*Shape of flower, side view.*—The upper portion is flat. The lower portion is concave.

Petalage: Under normal conditions, flowers have about 40 petals total, 3 to 5 of which are petaloids.

General tonality of flower: Open flowers are Red Group 46B.

Petal color:

*Upon opening, petals.*—Upper surface: Red Group 46B. Lower surface: Red Group 46A.

*Basal petal spots, upon opening.*—Upper surface: Yellow Group 9B. Lower surface: White Group 155A.

*After opening, petals.*—Upper surface: Red Group 46B. Lower surface: Red Group 46A.

*Basal petal spots, after opening.*—Upper surface: Yellow Group 9B. Lower surface: White Group 155A.

Petals:

*Petal reflex.*—Somewhat reflexed.

*Margin.*—Entire and uniform. Moderate undulations.

*Shape.*—Generally rounded. Apex shape: Rounded. Base shape: Acute.

*Size.*—30 mm (l)×28 mm (w).

*Texture.*—Smooth.

*Thickness.*—Average.

Petaloids:

*Size.*—16 mm (l) by 12 mm (w).

*Quantity.*—3 to 5.

*Shape.*—Elliptic.

*Color.*—Upper surface is Red Group 46B. Lower surface is Red Group 46A. Petaloid basal spots are Yellow Group 9B on the upper surface, White Group 155A lower surface.

Reproductive organs:

*Pollen.*—None observed.

*Anthers.*—Size: 1 mm in length. Color: Yellow Group 11B. Quantity: 35 on average.

*Filaments.*—Color: Yellow-Orange Group 23C. Length: 4 mm.

*Pistils.*—Length: 4 mm. Quantity: 20 on average.

*Stigmas.*—Color: Green-White Group 157A.

*Styles.*—Color: Green-White Group 157A.

*Location of stigmas.*—Level in location relative to the length of the filaments and the height of the anthers.

*Hips.*—None Observed.

Plant

Plant growth: Upright, bushy. Plants are 20- 25 cm in height, and 20 cm wide.

Stems:

*Color.*—Juvenile growth: Yellow-Green Group 144B with intonations of Greyed-Purple Group 184B. Mature growth: Yellow-Green Group 144B.

*Length.*—On average, canes are 15 cm from the base of the plant to the flowering portion.

*Diameter.*—4 mm.

*Internodes.*—On mature canes, there is an average distance of 25 mm between nodes.

*Surface texture.*—Young wood: Smooth. Older wood: Smooth.

Long prickles: None observed.

Plant foliage:

*Compound leaf.*—80 mm (l)×45 (w).

*Quantity.*—4 leaves per 10 cm of stem on average.

*Leaf bearing angle to the stem.*—60 degrees.

*Color of juvenile foliage.*—Upper side: Yellow-Green Group 152A with intonations of Greyed-Red Group 178B. Lower side: Yellow-Green Group 146B.

*Color of mature foliage.*—Upper side: Yellow-Green Group 147A. Lower side: Yellow-Green Group 146A.

Plant leaves and leaflets:

*Stipules.*—Size: 10 mm long, 2 mm wide. Quantity: 2 per compound leaf. Shape: Linear, slightly broad based with outward extending apices. Margins: Entire. Color: Yellow-Green Group 147A with intonations of Greyed-Red Group 178A.

*Petiole.*—Length: 10 to 20 mm. Diameter: 1 mm.

*Upper surface*.—Color: Greyed-Purple Group 187B.

*Lower surface*.—Color: Yellow-Green Group 144A.

*Rachis*.—Length: 15 to 20 mm. Upper surface: Color: Greyed-Purple Group 187B.

*Lower surface*.—Color: Yellow-Green Group 144A. Observations: Small prickles.

*Leaflet*.—Quantity: Normally 5 to 7 leaflets. Margins: Serrated. Size: On average terminal leaflets are 35 mm long, 20 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah071', substantially as illustrated and described herein, due to its abundant red flowers, disease resistance, and extended period of bloom.

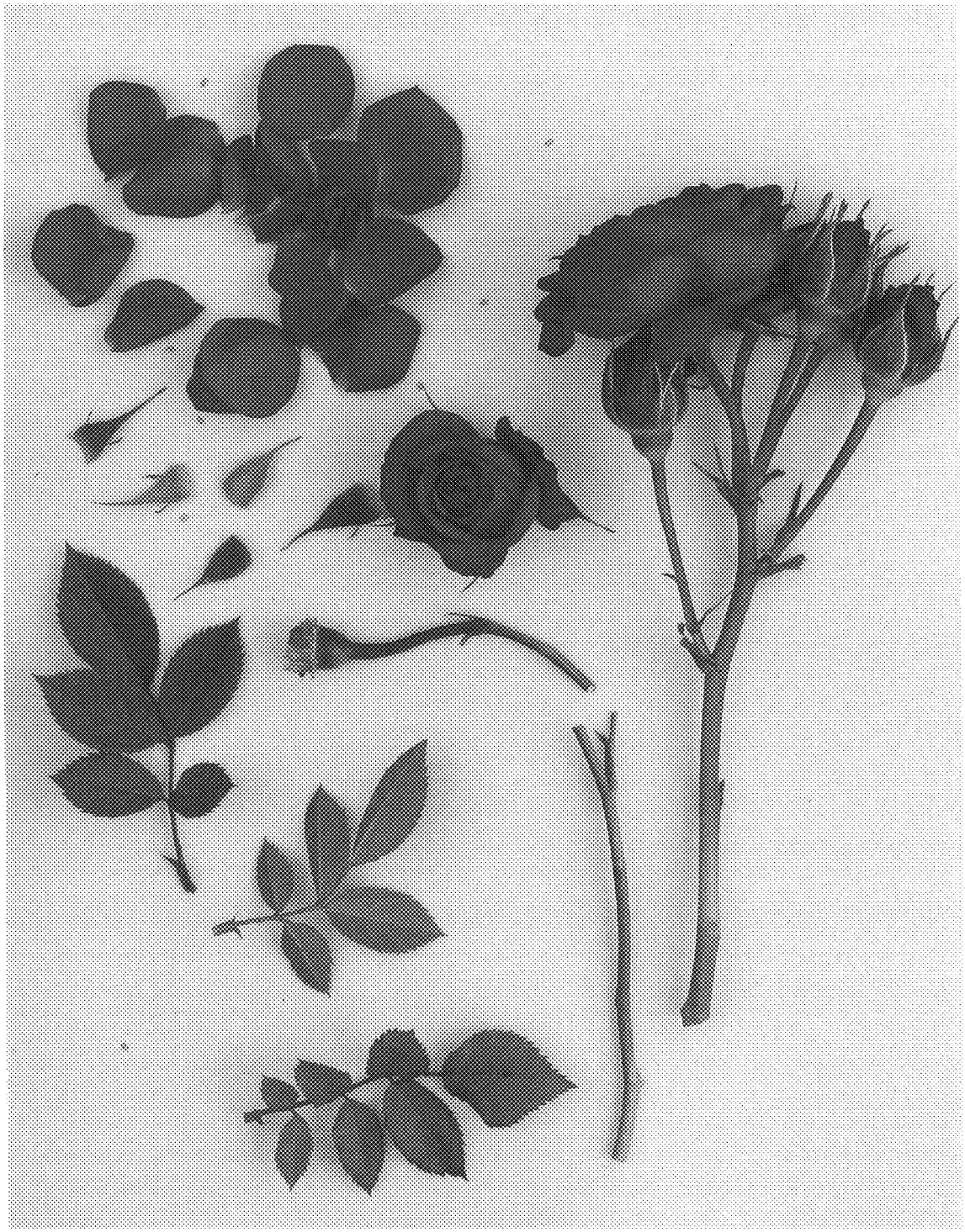

* * * * *